(12) United States Patent
Kuwano

(10) Patent No.: US 8,936,752 B2
(45) Date of Patent: Jan. 20, 2015

(54) SAMPLE ANALYZER AND SAMPLE PROCESSING APPARATUS

(75) Inventor: Keisuke Kuwano, Kobe (JP)

(73) Assignee: Sysmex Corporation, Hyogo (JP)

( * ) Notice: Subject to any disclaimer, the term of this patent is extended or adjusted under 35 U.S.C. 154(b) by 346 days.

(21) Appl. No.: 13/308,073

(22) Filed: Nov. 30, 2011

(65) Prior Publication Data
US 2012/0141326 A1    Jun. 7, 2012

(30) Foreign Application Priority Data

Dec. 1, 2010    (JP) .................................. 2010-268715

(51) Int. Cl.
*G01N 21/00* (2006.01)
*C12M 1/36* (2006.01)
*G01N 35/00* (2006.01)
*C12M 1/34* (2006.01)
*G01N 31/00* (2006.01)
*G01N 35/02* (2006.01)

(52) U.S. Cl.
CPC ...... G01N 35/00732 (2013.01); G01N 35/0092 (2013.01); *G01N 35/026* (2013.01)
USPC ................... 422/67; 422/62; 422/63; 422/64; 422/65; 422/66; 435/286.1; 435/286.2; 435/287.1

(58) Field of Classification Search
None
See application file for complete search history.

(56) References Cited

U.S. PATENT DOCUMENTS

2009/0325274 A1 *  12/2009  Hamada et al. ............ 435/286.2

FOREIGN PATENT DOCUMENTS

JP            3-183955 A        8/1991

* cited by examiner

*Primary Examiner* — Neil N Turk
(74) *Attorney, Agent, or Firm* — Sughrue Mion, PLLC

(57) ABSTRACT

A sample analyzer is disclosed. The sample analyzer comprises: a reader for reading ID of a sample from a sample container; an aspirator that aspirates a sample in a sample container; an analyzing section that analyzes the aspirated sample; a manual input receiver for receiving a manual input of an ID of a sample; an start instruction receiver for receiving a start instruction to cause the aspirator to aspirate a sample; and a controller. When receiving the start instruction without receiving the manual input, the controller controls the reader to read an ID from a sample container and then controls the aspirator to aspirate the sample from the sample container. When receiving the start instruction after receiving the manual input, the controller controls the aspirator to aspirate a sample without reading of an ID of the sample.

7 Claims, 13 Drawing Sheets

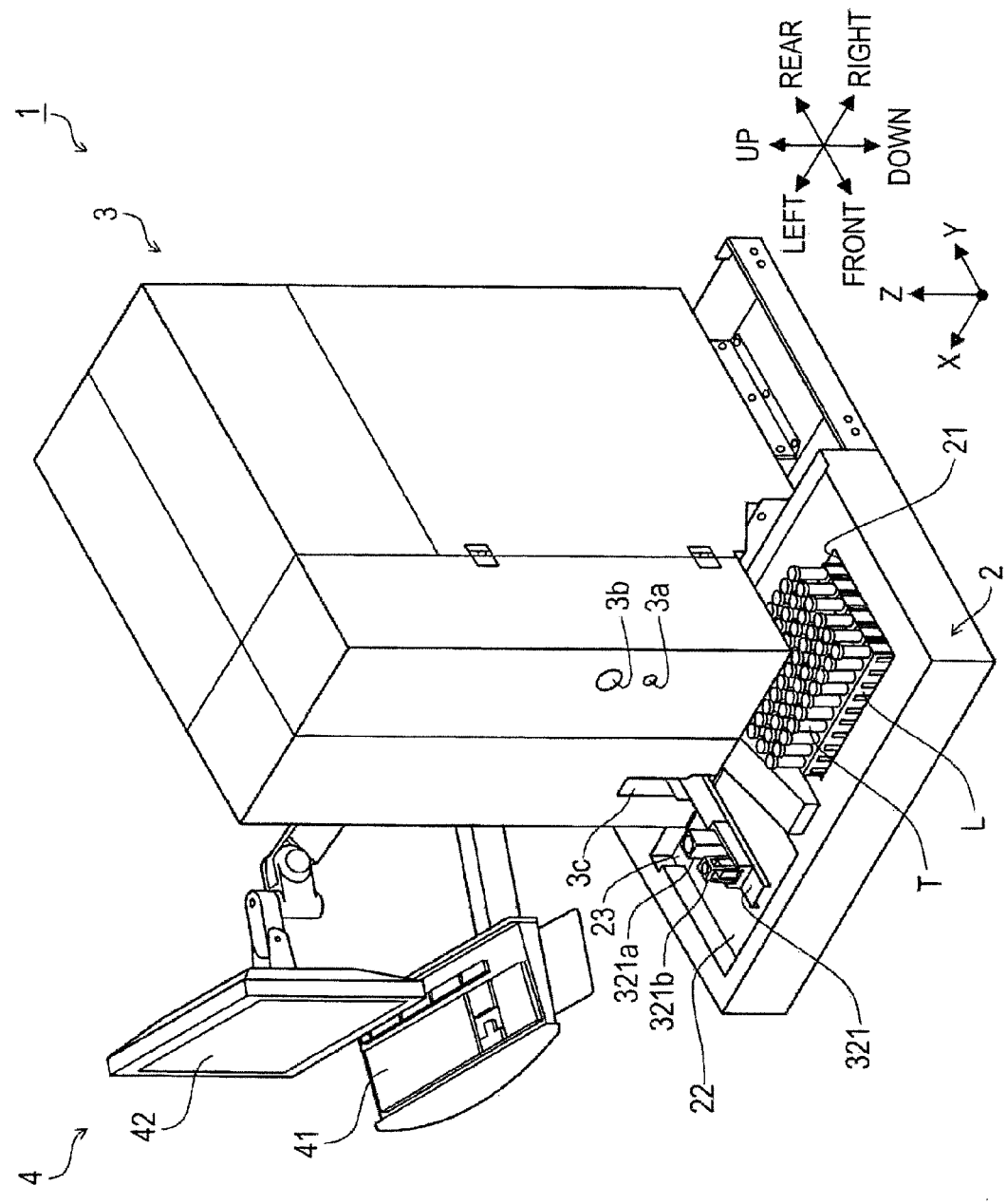

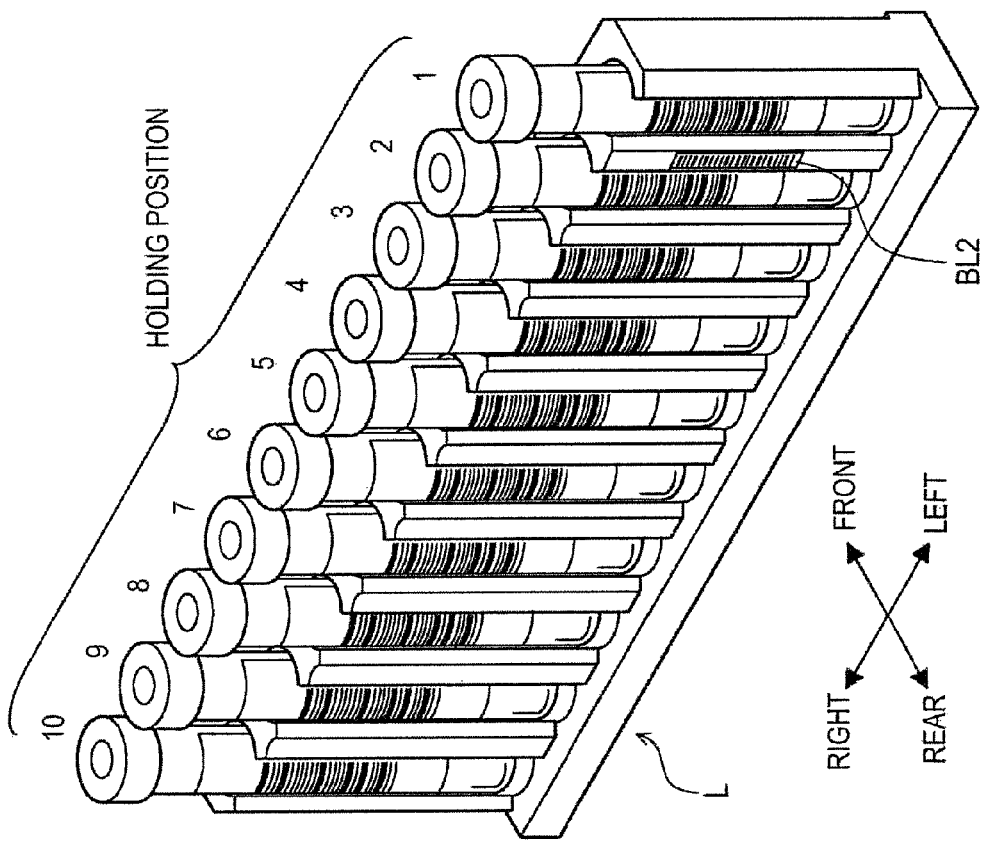
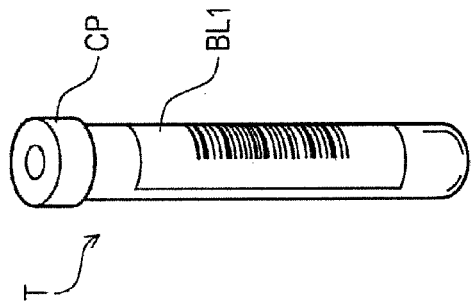
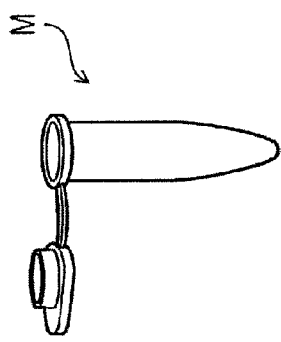

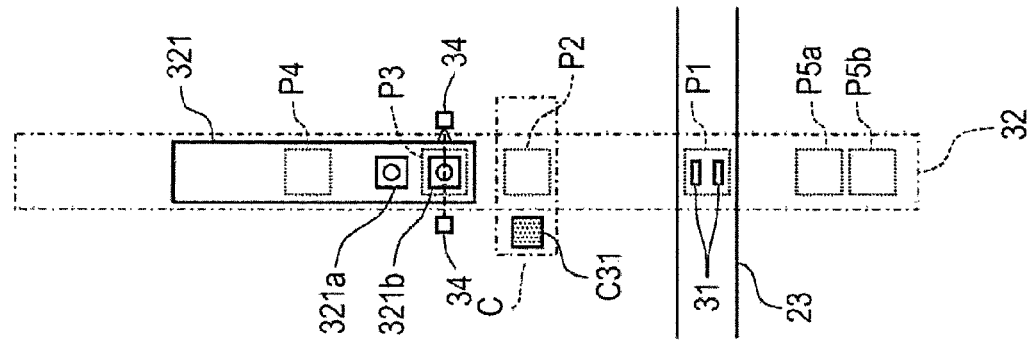
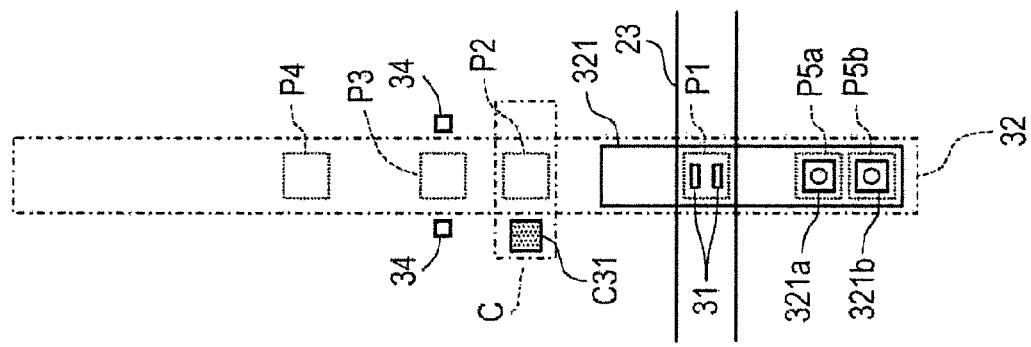
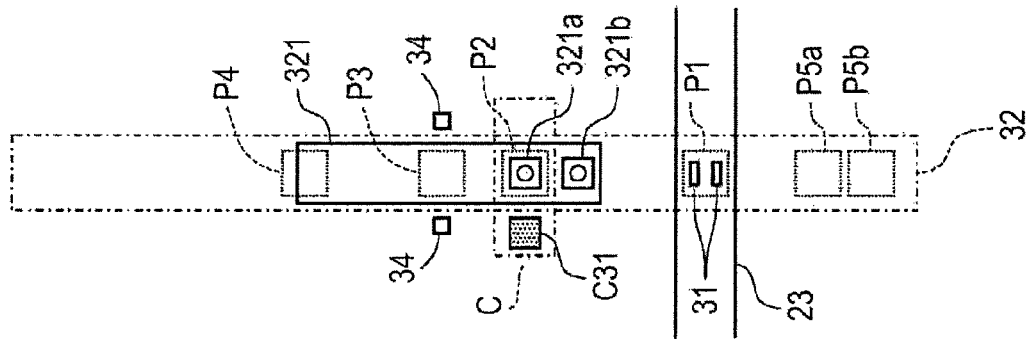
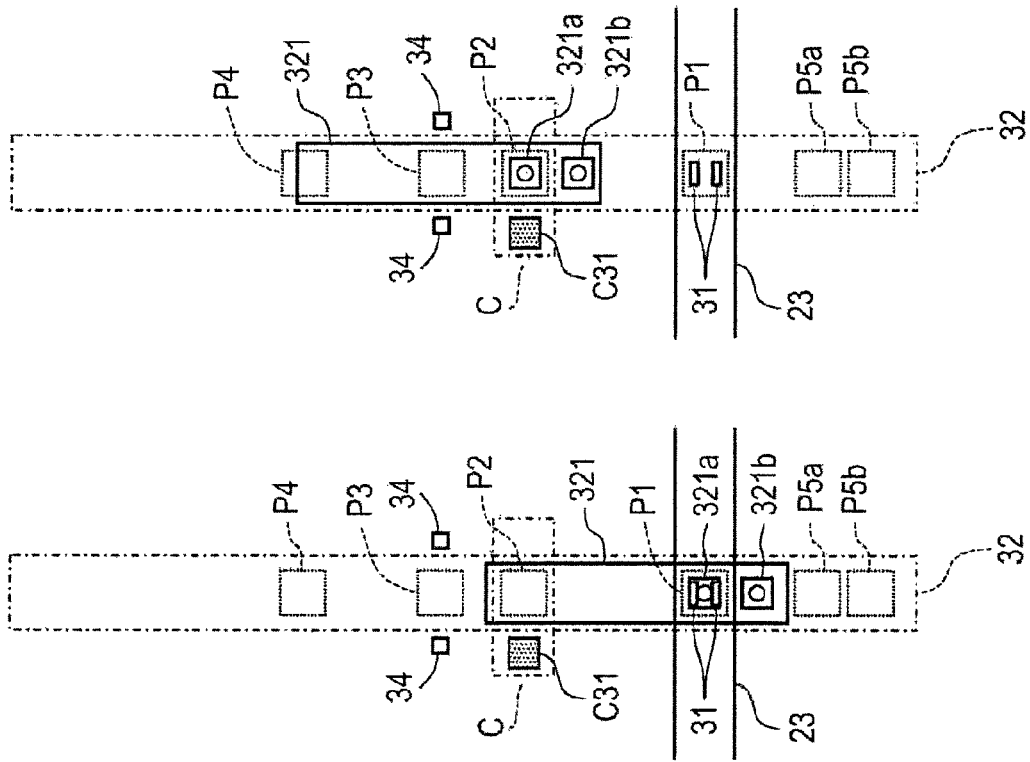

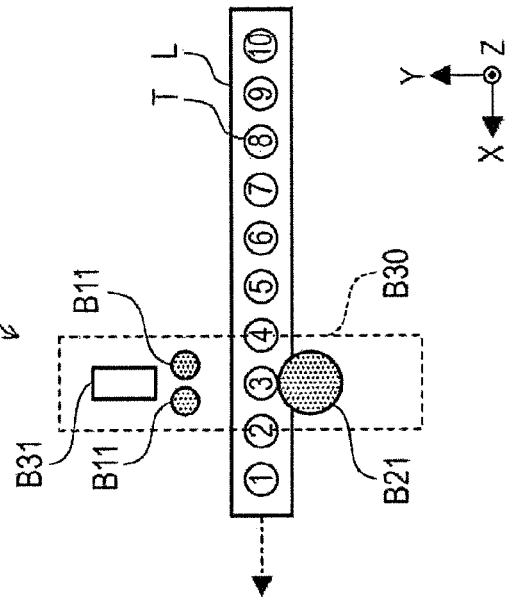
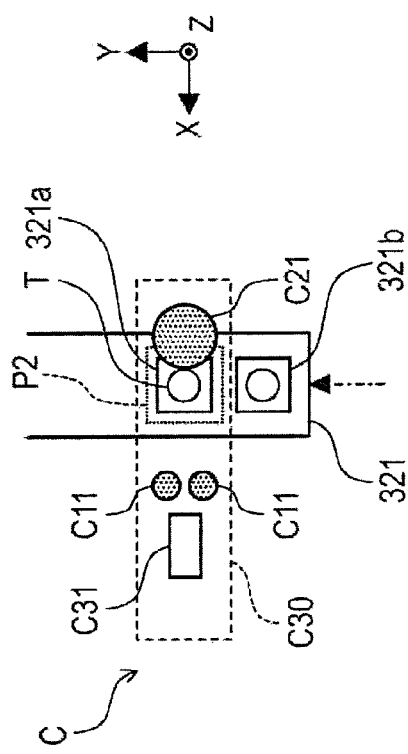
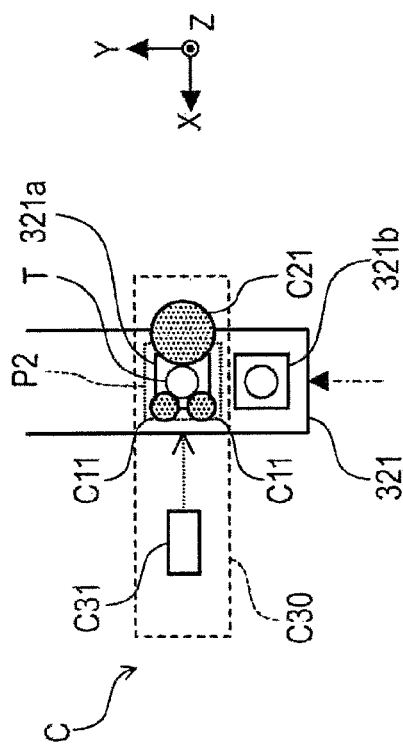

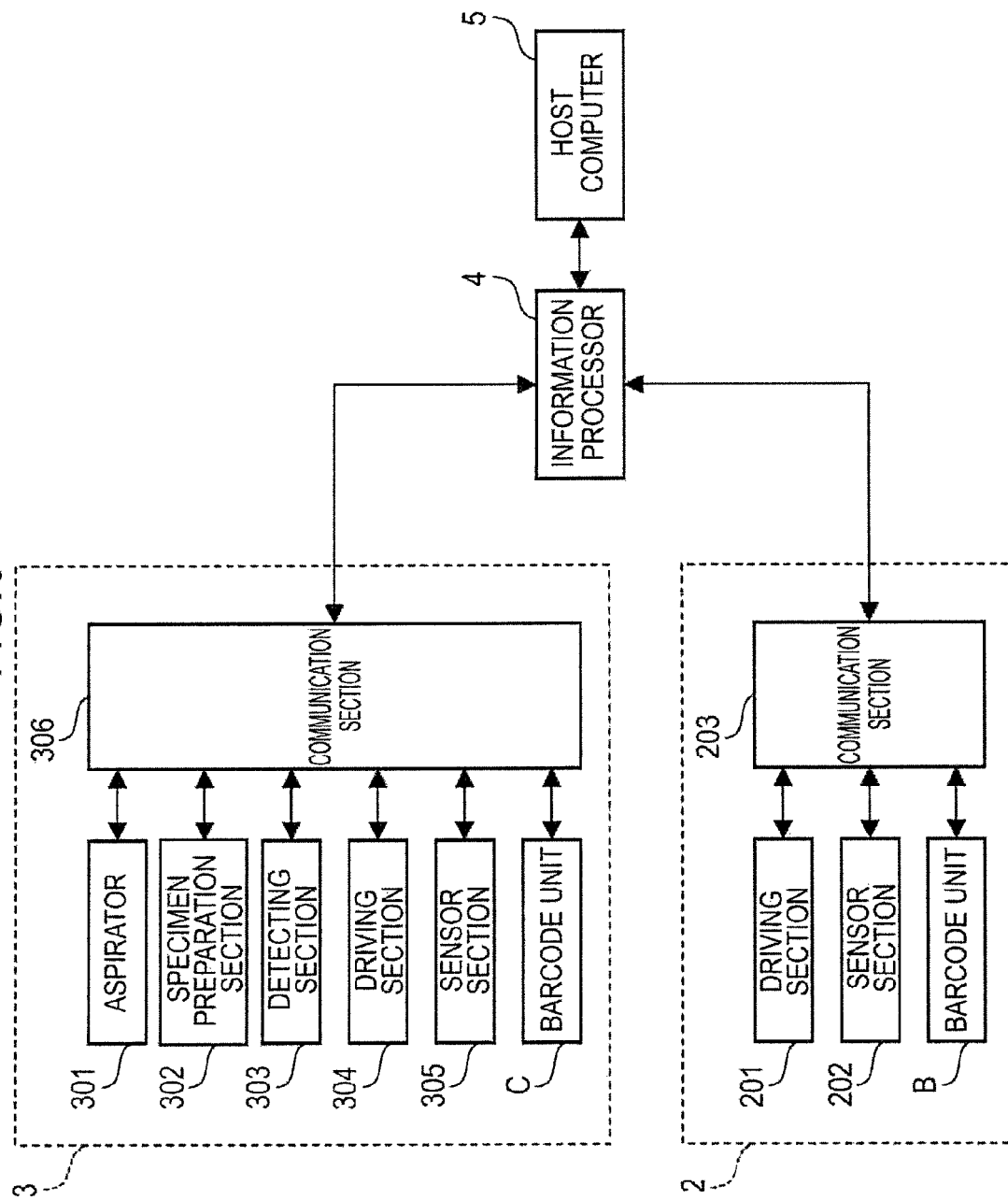

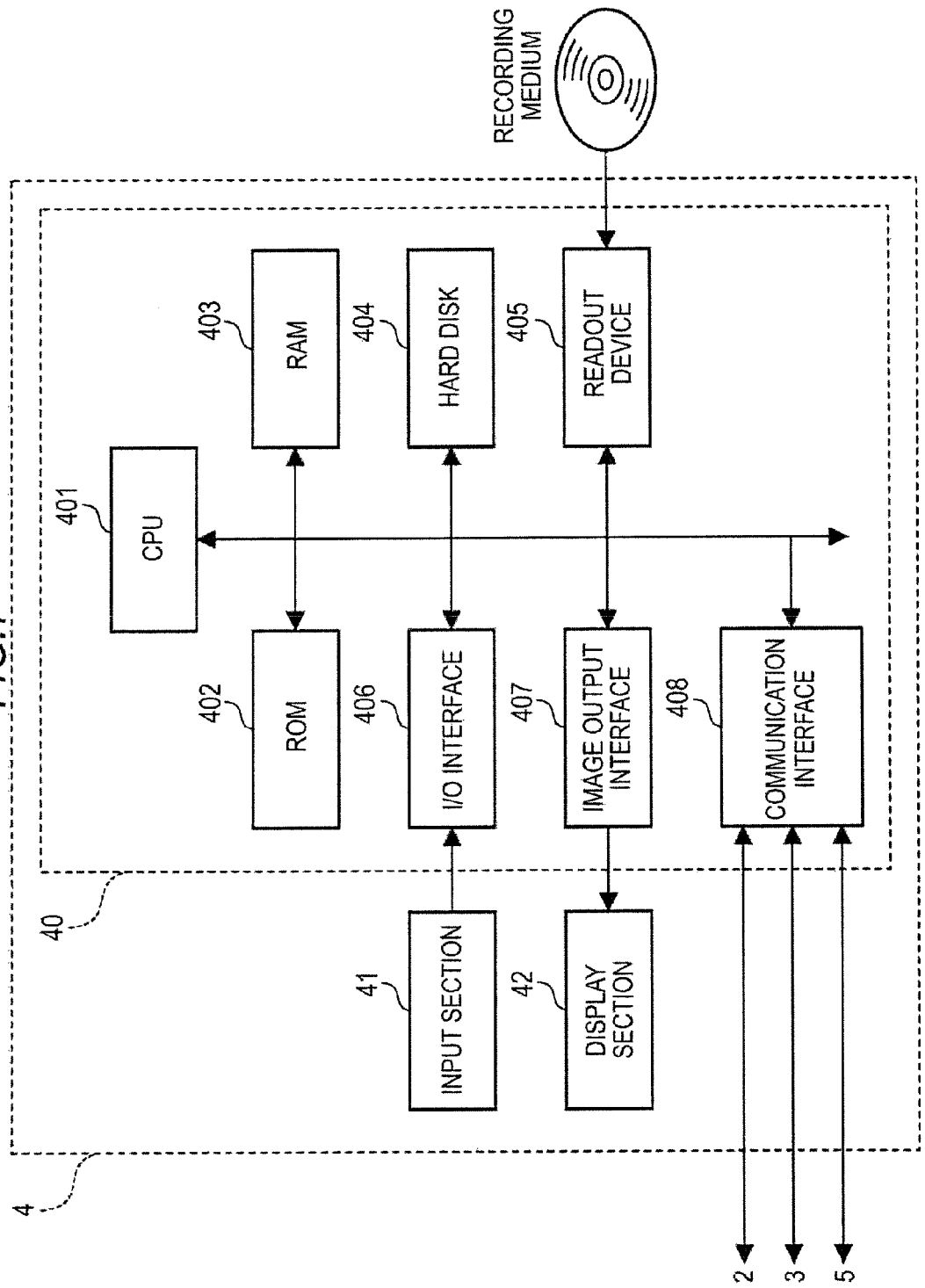

SAMPLE ANALYZER AND SAMPLE PROCESSING APPARATUS

FIELD OF THE INVENTION

The present invention relates to a sample analyzer which analyzes a sample in a sample container. The present invention also relates to a sample processing apparatus which processes a sample contained in a sample container.

BACKGROUND

Currently, sample processing apparatuses for processing a clinical sample such as blood and urine are used in medical facilities.

U.S. Patent Application Publication 2009-0325274 discloses a sample analyzer in which a rack which holds sample containers containing a normal sample is transported to sequentially take the sample containers into the apparatus and measure the samples therein, and a priority sample to be measured in priority to a normal sample is allowed to interrupt the measurement of the normal sample so as to be measured. In this apparatus, when a normal sample is measured, the sample container is taken into the apparatus to read a barcode adhered to the sample container by a barcode reader provided in the apparatus. In addition, in this apparatus, when a priority sample is measured, a user manually inputs the sample number and the measurement items of the priority sample from a priority sample measurement instruction screen.

The sample container containing a priority sample is not limited to those with no barcode adhered thereto, and may have a barcode adhered thereto. However, in the sample analyzer of U.S. Patent Application Publication 2009-0325274, when a priority sample is measured, the sample number thereof is required to be manually input. Even if the priority sample has a barcode adhered thereto, the barcode cannot be read by the barcode reader. Therefore, a technology is desired which allows identification data of the priority sample to be more smoothly input.

SUMMARY OF THE INVENTION

A first aspect of the present invention is a sample analyzer comprising: a reader for reading identification data (ID) of a sample from a sample container; an aspirator that aspirates a sample in a sample container; an analyzing section that analyzes the aspirated sample; a manual input receiver for receiving a manual input of an ID of a sample; an start instruction receiver for receiving a start instruction to cause the aspirator to aspirate a sample; and a controller, wherein when receiving the start instruction without receiving the manual input, the controller controls the reader to read an ID from a sample container and then controls the aspirator to aspirate the sample from the sample container, and when receiving the start instruction after receiving the manual input, the controller controls the aspirator to aspirate a sample without reading of an ID of the sample.

A second aspect of the present invention is a sample processing apparatus comprising: a holder for holding a sample container; a reader that reads identification data (ID) from a sample container held by the holder at a reading position; a display; a first instruction receiver for receiving a first instruction to cause the display to show an input screen for inputting an ID of a sample container; a transfer section that transfers the holder from a placing position where an operator sets a sample container onto the holder via the reading position to an aspirating position; a sample processing section that aspirates a sample in a sample container at the aspirating position and processes the aspirated sample; a second instruction receiver for receiving a second instruction to cause the sample processing section to start sample processing; and a controller, wherein when receiving the second instruction, the controller controls the reader to read an ID of a sample container on a path of transferring the sample container, when receiving the first instruction, the controller receives the second instruction after receiving the input of the ID from the input screen, and then transfers the holder to the aspirating position with skipping the reading of the ID.

BRIEF DESCRIPTION OF THE DRAWINGS

FIG. 1 is a perspective view showing the appearance of a sample processing apparatus according to an embodiment.

FIG. 2 shows the configurations of a sample container, a sample rack, and a tube according to the embodiment.

FIG. 4 shows plan views showing the vicinity of a sample container transport section according to the embodiment.

FIG. 5 shows views illustrating a reading operation by barcode units according to the embodiment.

FIG. 6 is a view showing the configurations of the transport unit and the measuring unit according to the embodiment.

FIG. 7 is a view showing the configuration of an information processor according to the embodiment.

DETAILED DESCRIPTION OF THE INVENTION

Figure 3:
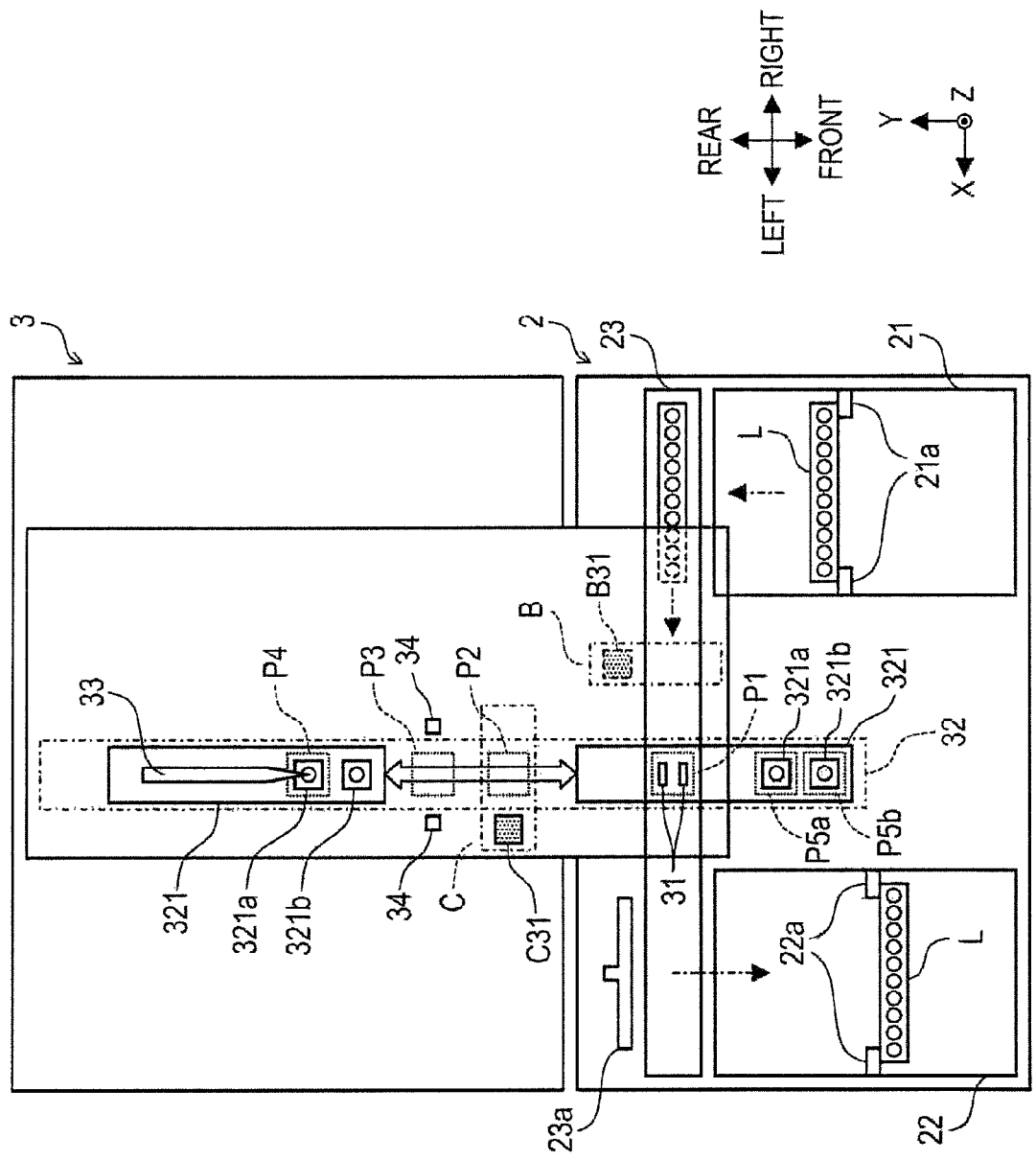
FIG. 3 is a plan view showing the configuration when a transport unit and a measuring unit according to the embodiment are viewed from the upper side.

This embodiment relates to a sample analyzer for examining and analyzing blood to which the invention is applied.

Hereinafter, a sample analyzer according to this embodiment will be described with reference to the drawings.

FIG. 1 is a perspective view showing the appearance of a sample analyzer 1. The sample analyzer 1 according to this embodiment is constituted of a transport unit 2, a measuring unit 3, and an information processor 4. In addition, the sample analyzer 1 of this embodiment is connected to a host computer 5 (see FIG. 6) via a communication network so as to communicate therewith.

The transport unit 2 is disposed ahead of the measuring unit 3 and is provided with a right table 21, a left table 22, and a rack transport section 23 connecting the right table 21 to the left table 22. The right table 21 and the left table 22 can accommodate a plurality of sample racks L capable of holding ten sample containers T.

FIGS. 2A and 2B are views showing the configurations of a sample container T and a sample rack L. FIG. 2A is a perspective view showing the appearance of a sample container T, and FIG. 2B is a perspective view showing the appearance of a sample rack L in which ten sample containers T are held. In FIG. 2B, directions (the forward and backward, and rightward and leftward directions in FIG. 1) in which the sample rack L is placed in the transport unit 2 are also shown.

Referring to FIG. 2A, the sample container T is a tubular container made of glass or a synthetic resin having translucency, and the upper end thereof is opened. A blood sample which is whole blood collected from a patient is contained therein and the opening at the upper end is sealed by a cap section CP. A barcode label BL1 is adhered to a side surface of the container T. A barcode showing a sample ID is printed on the barcode label BL1.

Referring to FIG. 2B, in the sample rack L, ten holders are formed at holding positions 1 to 10 as shown in the drawing so as to hold ten containers T in parallel in a vertical state (erect state). In addition, a barcode label BL2 is adhered to a rear side surface of the sample rack L as shown in the drawing. A barcode showing a rack ID is printed on the barcode label BL2.

FIG. 2C is a view showing the configuration of a tube M for accommodating a tiny amount of a sample. The tube M is configured to be smaller than a sample container T, and is set in a sample container setting section 321b when a priority sample to be described later is measured. A barcode label is not adhered to the tube M.

Returning to FIG. 1, the transport unit 2 accommodates a sample rack L which is placed on the right table 21 by a user. In addition, the transport unit 2 transports the sample rack L which is accommodated on the right table 21, and positions the sample rack L at a predetermined position of the rack transport section 23 so as to supply sample containers T to the measuring unit 3. Furthermore, the transport unit 2 transports the sample rack L positioned on the rack transport section 23, and collects the sample rack L to the left table 22.

The measuring unit 3 is provided with an opening button 3a, a measurement start button 3b, a hand section 31 (see FIG. 3) capable of grasping a sample container T, and a base 321. In the base 321, a sample container setting section 321a capable of setting a sample container T and a sample container setting section 321b capable of setting a tube M are installed.

The measuring unit 3 processes a sample container T which is positioned on the rack transport section 23 of the transport unit 2 disposed ahead of the measuring unit 3. That is, the measuring unit 3 takes a sample container T out of a sample rack L by the hand section 31 (see FIG. 3) at the predetermined position of the rack transport section 23, and measures the sample contained in the sample container T in the measuring unit 3. When the measurement is completed, the measuring unit 3 returns the sample container T to the original holder of the sample rack L. Hereinafter, the measurement which is performed by sequentially taking out sample containers T transported by the transport unit 2 from the predetermined position of the rack transport section 23 by the hand section 31 as above will be referred to as "sampler measurement".

When a user presses the opening button 3a, the base 321 protrudes forward from a front surface of the measuring unit 3 via an opening section 3c formed on a front surface of the measuring unit 3, and the sample container setting sections 321a and 321b are positioned ahead of the front surface of the measuring unit 3. The user sets a sample container T or a tube M in the sample container setting section 321a or 321b and presses the measurement start button 3b to interrupt the sampler measurement, whereby a sample to be measured urgently can be preferentially measured. Hereinafter, the measurement which interrupts the sampler measurement to be preferentially performed as above will be referred to as "priority sample measurement".

The information processor 4 is provided with an input section 41 and a display section 42. In addition, the information processor 4 is connected to the transport unit 2, the measuring unit 3, and the host computer 5 (see FIG. 6) via a communication network so as to communicate therewith.

The information processor 4 controls the operations of the transport unit 2 and the measuring unit 3. In addition, the information processor 4 inquires of the host computer 5 (see FIG. 6) about a measurement order when a barcode reader B31 (see FIG. 3) in the transport unit 2 and a barcode reader C31 (see FIG. 3) in the measuring unit 3 read a sample ID. Furthermore, the information processor 4 performs analysis based on the result of the measurement performed by the measuring unit 3, and transmits the analysis result to the host computer 5 (see FIG. 6).

FIG. 3 is a plan view showing the configuration when the transport unit 2 and the measuring unit 3 are viewed from the upper side. FIG. 4 shows plan views showing the vicinity of a sample container transport section 32.

First, the sampler measurement will be described with reference to FIGS. 3, 4(a), and 4(b).

The front side surface of a sample rack L which is placed on the right table 21 is pressed by a rack input mechanism 21a, so that the sample rack L is transported to the right end position of the rack transport section 23. The sample rack L which is positioned at the right end position of the rack transport section 23 is transported in the leftward direction by a belt (not shown) of the rack transport section 23.

A barcode unit B provided with the barcode reader B31 is installed in the vicinity of the center of the rack transport section 23. When a holder of the sample rack L is positioned ahead of the barcode reader B31, the barcode unit B determines whether or not the positioned holder holds a sample container T. When this holder holds a sample container T, the barcode reader B31 reads a sample ID of the sample container T. In addition, when a barcode label BL2 of the sample rack L is positioned ahead of the barcode reader B31, the barcode reader B31 reads a rack ID of the sample rack L. The readout operation by the barcode unit B will be described later with reference to FIG. 5(c).

The sample container T whose sample ID has been read by the barcode reader B31 is further transported in the leftward direction to be positioned at a take-in position P1. At the take-in position P1, the hand section 31 is installed in the measuring unit 3 to be movable in the vertical direction (Z-axis direction). The sample container T positioned at the take-in position P1 is grasped by the hand section 31, and taken out of the sample rack L in the upward direction (Z-axis positive direction). The transport of the sample rack L is put on hold during the period in which the sample container T returns to the sample rack L.

The sample container transport section 32 is formed of the base 321 having the sample container setting sections 321a and 321b installed therein, and a mechanism (not shown) for moving the base 321 forward and backward within an area surrounded by the alternated long and short dash line. Such a mechanism includes a belt which moves forward and backward and a stepping motor for moving the belt. The base 321 is installed on the belt, and configured to move forward and backward in accordance with the driving of the stepping motor.

When the sample container T grasped by the hand section 31 is lifted above the sample container transport section 32, the base 321 is moved to position the sample container setting section 321a at the take-in position P1. FIG. 4A shows the position of the base 321 at this time. In this state, the hand section 31 is moved in the downward direction (Z-axis negative direction), and the sample container T grasped by the hand section 31 is set in the sample container setting section 321a.

Next, the base 321 is moved backward, and the sample container setting section 321a is positioned at a position (barcode reading position P2) opposed to the barcode reader C31 of the barcode unit C. FIG. 4B shows the position of the base 321 at this time. In this state, the barcode unit C determines whether or not the sample container T is set in the sample container setting section 321a, and when the sample container T is set, the sample ID of the sample container T is read. The reading operation by the barcode unit C will be described later with reference to FIGS. 5A and 5B.

Next, the base 321 is moved backward and the sample container setting section 321a is positioned at a position (aspirating position P4) immediately below a piercer 33. Here, the piercer 33 is moved in the downward direction, and the sample is aspirated from the sample container T positioned at the aspirating position P4. The aspirated sample is mixed with a reagent in a specimen preparation section 302 to be described later to produce a measurement specimen. In a detecting section 303, blood cells which are included in the measurement specimen are detected and counted.

When the aspiration of the sample by the piercer 33 ends, the base 321 is moved forward, and the sample container setting section 321a is positioned at the take-in position P1 again. At the take-in position P1, the sample container T is taken out of the sample container setting section 321 in the upward direction by the hand section 31. In this state, the base 321 is moved backward, and then the hand section 31 is moved in the downward direction (Z-axis negative direction). The sample container T returns to the original holder of the sample rack L which is positioned on the rack transport section 23.

In this manner, when the measurement of the samples of all of the sample containers T held in the sample rack L ends, the sample rack L is sent to the left end position of the rack transport section 23. Then, the sample rack L is pushed to the rear position of the left table 22 by a rack pushing mechanism 23a. The sample rack L positioned at the rear position of the left table 22 is transported to the front of the left table 22 by a rack input mechanism 22a. In this manner, when the measurement process of all of the sample racks L on the right table 21 ends, the sampler measurement ends.

Next, the priority sample measurement will be described with reference to FIGS. 3 and 4B to 4D.

When a user presses the opening button 3a (see FIG. 1), the base 321 is moved forward, and the sample container setting sections 321a and 321b are positioned at priority sample setting positions P5a and P5b, respectively. FIG. 4C shows the position of the base 321 at this time. In this state, the user sets a sample container T or a tube M containing a sample to be preferentially measured in the sample container setting section 321a or 321b.

When the measurement start button 3b (see FIG. 1) is pressed to start the measurement of the priority sample, it is determined whether or not the sample container T and the tube M are held in the sample container setting sections 321a and 321b. Whether or not the sample container T is held in the sample container setting section 321a is determined by the barcode unit C in the state of FIG. 4B as in the case of the sampler measurement. Whether or not the tube M is held in the sample container setting section 321b is determined by a sensor 34. That is, the base 321 is moved, and the sample container setting section 321b is positioned at a position (sensor reading position P3) corresponding to the sensor 34. The sensor 34 is a transmission-type sensor formed of a light-emitting section and a light-receiving section. FIG. 4D shows the position of the base 321 at this time. In this state, the sensor 34 determines whether or not the tube M is set in the sample container setting section 321b. When samples are set in both of the sample container setting sections 321a and 321b, an error screen is displayed on the display section 42, and as shown in FIG. 4C, the base 321 is positioned ahead of the measuring unit 3.

When the sample container T is set in the sample container setting section 321a, the barcode reader C31 reads the sample ID of the sample container T in the state of FIG. 4B as in the case of the above-described sampler measurement. When the tube M is set in the sample container setting section 321b, the sample ID of the tube M is input by a user via the input section 41.

Next, the base 321 is moved backward, and the sample container T or the tube M is positioned at the position (aspirating position P4) immediately below a piercer 33. Here, the piercer 33 is moved in the downward direction, and the sample is aspirated from the sample container T or the tube M positioned at the aspirating position P4.

When the aspiration of the sample by the piercer 33 ends, the base 321 is moved forward, and the sample container setting sections 321a and 321b are positioned at the priority sample setting positions P5a and P5b, respectively. A user takes the sample container T or the tube M in which the aspiration has ended out of the sample container setting section 321a or 321b. In this manner, the priority sample measurement ends.

FIG. 5 shows views illustrating the reading operation by the barcode units B and C. FIGS. 5A and 5B are plan views showing the configuration of the barcode unit C, and FIG. 5C is a plan view showing the configuration of the barcode unit B.

Referring to FIG. 5A, the barcode unit C is constituted of two rollers C11, a roller C21, a base C30, and the barcode reader C31. The two rollers C11 are configured to be rotated around the Z axis, and are configured to be movable in the X-axis direction on the base C30. The roller C21 is configured to be rotated and driven around the Z axis, and is fixed onto the base C30. The barcode reader C31 is fixed to the base C30 and reads a barcode which is positioned on the right side (Z-axis negative direction).

When the barcode reader C31 reads the sample ID of a sample container T which is positioned on the right side, as shown in FIG. 5B, the tow rollers C11 are moved to the right side to be brought into contact with a side surface of the sample container T. At this time, when the rollers C11 are movable to the right side by a predetermined amount or more without being brought into contact with the sample container T, it is determined that the sample container T is not held in the sample container setting section 321a. In this case, a sensor (not shown) detects that the rollers C11 are moved to the right side of the position where the rollers C11 are brought into contact with the sample container T. On the other hand, when the two rollers C11 is brought into contact with the sample container T, and does not move to the right side by a predetermined amount or more, it is determined that the sample container T is held in the sample container setting section 321a.

When it is determined that the sample container T is held in the sample container setting section 321a, the barcode reader C31 reads the sample ID of the sample container T. That is, in the state shown in FIG. 5B, the rollers C11 is rotated and driven, and thus the sample container T is rotated around the Z axis, and the barcode reader C31 reads the barcode label BL1 during the rotation of the sample container T. Accordingly, even when the barcode label BL1 of the sample container T is positioned on the opposite side to the barcode reader C31, it is possible to read the sample ID of the sample container T.

Referring to FIG. 5C, as in the case of the barcode unit C, the barcode unit B is constituted of two rollers B11, a roller B21, a base B30, and the barcode reader B31. The two rollers B11 are configured to be rotated around the Z axis, and are configured to be movable in the Y-axis direction on the base B30. The roller B21 is configured to be rotated and driven around the Z axis, and is fixed onto the base B30. The barcode reader B31 is fixed to the base B30 and reads a barcode which is positioned anteriorly (Y-axis negative direction).

When the barcode unit B is configured as above, as in the case of the barcode unit C, the barcode unit B determines whether or not the sample container T is held in a holder of the sample rack L positioned ahead of the barcode reader B31. In addition, the sample ID of the sample container T positioned ahead of the barcode reader B31 and the rack ID of the sample rack L are read.

FIG. 6 is a schematic view showing the configurations of the transport unit 2 and the measuring unit 3.

The transport unit 2 is provided with a driving section 201, a sensor section 202, a communication section 203, and the barcode unit B.

The driving section 201 includes a mechanism for transporting a sample rack L in the transport unit 2, and the sensor section 202 includes a sensor for detecting a sample rack L in the transport unit 2. The barcode unit B includes a mechanism for driving the rollers B11 and B21 and the barcode reader B31.

The communication section 203 is connected to the information processor 4 so as to communicate therewith. The sections in the transport unit 2 are controlled by the information processor 4 via the communication section 203. In addition, the signals output from the sections in the transport unit 2 are transmitted to the information processor 4 via the communication section 203.

The measuring unit 3 is provided with an aspirator 301, a specimen preparation section 302, a detecting section 303, a driving section 304, a sensor section 305, a communication section 306, and the barcode unit C.

The aspirator 301 includes a mechanism which aspirates a sample contained in a sample container T or a tube M via the piercer 33. The specimen preparation section 302 is provided with a plurality of reaction chambers. The specimen preparation section 302 mixes and stirs the aspirated sample and a reagent in a reaction chamber to prepare a measurement specimen. The detecting section 303 measures the specimen prepared by the specimen preparation section 302.

The driving section 304 includes a mechanism for transporting a sample container T and a tube M in the measuring unit 3. Specifically, the driving section 304 includes a mechanism for driving the hand section 31 and a mechanism for driving the sample container transport section 32. The sensor section 305 includes a sensor for detecting a sample container T and a tube M in the measuring unit 3. Specifically, the sensor section 305 includes the sensor 34. In addition, the sensor section 305 includes a sensor which detects the pressing of the opening button 3a and the measurement start button 3b. The barcode unit C includes a mechanism for driving the rollers C11 and C21 and the barcode reader C31.

The communication section 306 is connected to the information processor 4 so as to communicate therewith. The sections in the measuring unit 3 are controlled by the information processor 4 via the communication section 306. In addition, the signals output from the sections in the measuring unit 3 are transmitted to the information processor 4 via the communication section 306.

FIG. 7 is a view showing the configuration of the information processor 4.

The information processor 4 is formed of a personal computer including a main body 40, the input section 41, and the display section 42. The main body 40 has a CPU 401, a ROM 402, a RAM 403, a hard disk 404, a readout device 405, an I/O interface 406, an image output interface 407, and a communication interface 408.

The CPU 401 executes computer programs which are stored in the ROM 402 and computer programs which are loaded in the RAM 403. The RAM 403 is used in the readout of computer programs which are recorded in the ROM 402 and the hard disk 404. In addition, the RAM 403 is also used as a work area of the CPU 401 when these computer programs are executed.

In the hard disk 404, various computer programs for execution by the CPU 401, such as operating systems and application programs, and data which are used to execute the computer programs, are installed. That is, in the hard disk 404, programs and the like to analyze the measurement result transmitted from the measuring unit 3 and perform display on the display section 42 on the basis of the analysis result are installed. In addition, in the hard disk 404, programs and the like for displaying a control menu screen D1 (see FIGS. 8A and 8B), a manual measurement screen D2 (see FIG. 8C), and error screens D31 to D34 (see FIGS. 12A to 12D) and receiving an input via the screens are installed.

The readout device 405 is constituted of a CD drive, a DVD drive or the like, and can read out computer programs and data recorded on recording mediums. The input section 41 formed of a mouse or a keyboard is connected to the I/O interface 406, and a user uses the input section 41 to input instructions and data to the information processor 4. The image output interface 407 is connected to the display section 42 constituted of a display or the like is connected to, and outputs a video signal according to image data to the display section 42.

The display section 42 displays an image based on the input video signal. The display section 42 displays various program screens in addition to the control menu screen D1 (see FIGS. 8A and 8B), the manual measurement screen D2 (see FIG. 8C), and the error screens D31 to D34 (see FIGS. 12A to 12D). In addition, using the communication interface 408, data transmission and reception to and from the transport unit 2, the measuring unit 3, and the host computer 5 is possible.

Figure 8C:
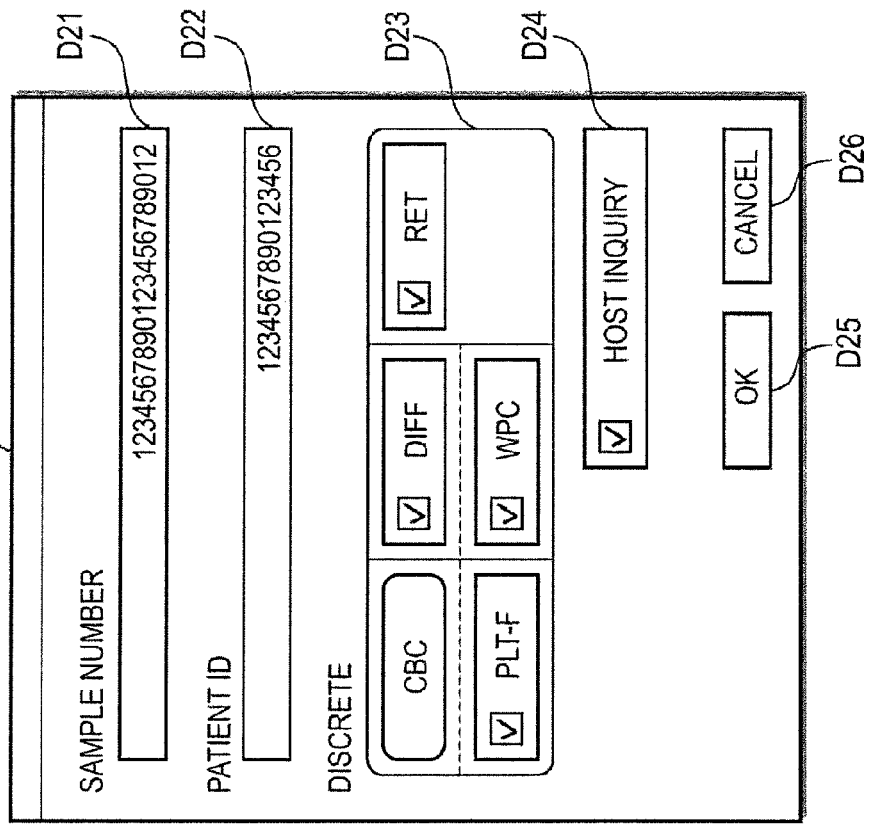
FIG. 8 show views showing a control menu screen and a manual measurement screen which are displayed on a display section of the information processor according to the embodiment.
Figure 8A:
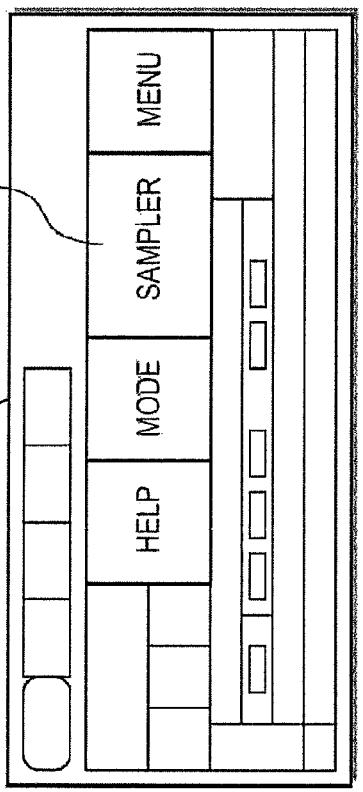
Figure 8B:
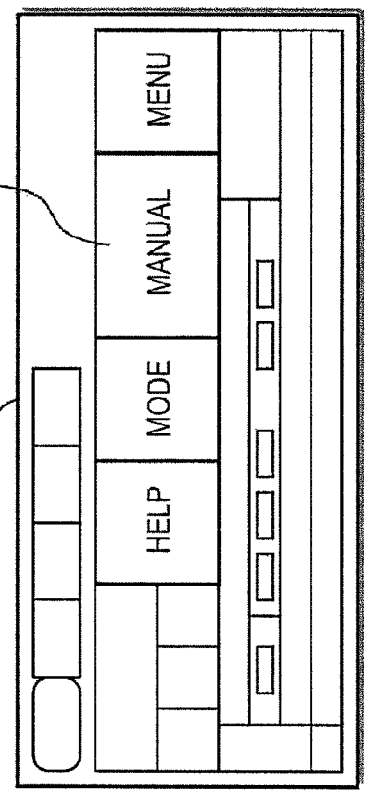

FIGS. 8A and 8B are views showing the control menu screen D1 which is displayed on the display section 42 of the information processor 4. The control menu screen D1 is always displayed in a corner of the display section 42.

Referring to FIG. 8A, the control menu screen D1 includes a sampler/manual button D11. When the sampler measurement is performed, the sampler/manual button D11 is displayed as "SAMPLER" as shown in FIG. 8A. When the opening button 3a is pressed and the sample container setting sections 321a and 321b are positioned ahead of the measuring unit 3, the sampler/manual button D11 is displayed as "MANUAL" as shown in FIG. 8B. In the case in which the sampler/manual button D11 is displayed as "MANUAL", when the sampler/manual button D11 is pressed, the manual measurement screen D2 shown in FIG. 8C is displayed.

FIG. 8C is a view showing the manual measurement screen D2 which is displayed on the display section 42 of the information processor 4.

The manual measurement screen D2 includes a sample number display region D21, a patient ID display region D22, a discrete display region D23, a host inquiry display region D24, an OK button D25, and a cancel button D26.

The same letter string as the sample ID of a barcode label BL1 is input to the sample number display region D21. A letter string for identifying a patient from which the sample has been collected is input to the patient ID display region D22. Measurement items including a check box are listed in the discrete display region D23, and by checking the check boxes of the measurement items, the content (measurement order) of the measurement which is subjected to the sample is designated. The host inquiry display region D24 is provided with a check box, and when this check box is checked, an inquiry is made to the host computer 5 about a measurement order on the basis of the sample number which is input to the sample number display region D21.

When the OK button D25 is pressed, the sample measurement is performed with the content set in the respective display regions of the manual measurement screen D2. That is, when the host inquiry display region D24 is not checked, the sample measurement is performed on the basis of the discrete display region D23. When the host inquiry display region D24 is checked, a measurement order corresponding to the sample number which is input to the sample number display region D21 is acquired from the host computer 5, and the sample measurement is performed on the basis of the acquired measurement order. When the cancel button D26 is pressed, the content set in the respective display regions of the manual measurement screen D2 is discarded and the manual measurement screen D2 is closed.

When the manual measurement screen D2 is used as above, the measurement of a sample which is contained in a sample container T without a barcode label BL1 adhered thereto and the measurement of a sample which is contained in a tube M can be performed in the same manner as in the measurement of a sample which is contained in a sample container T with a barcode label BL1 adhered thereto.

Figure 9:
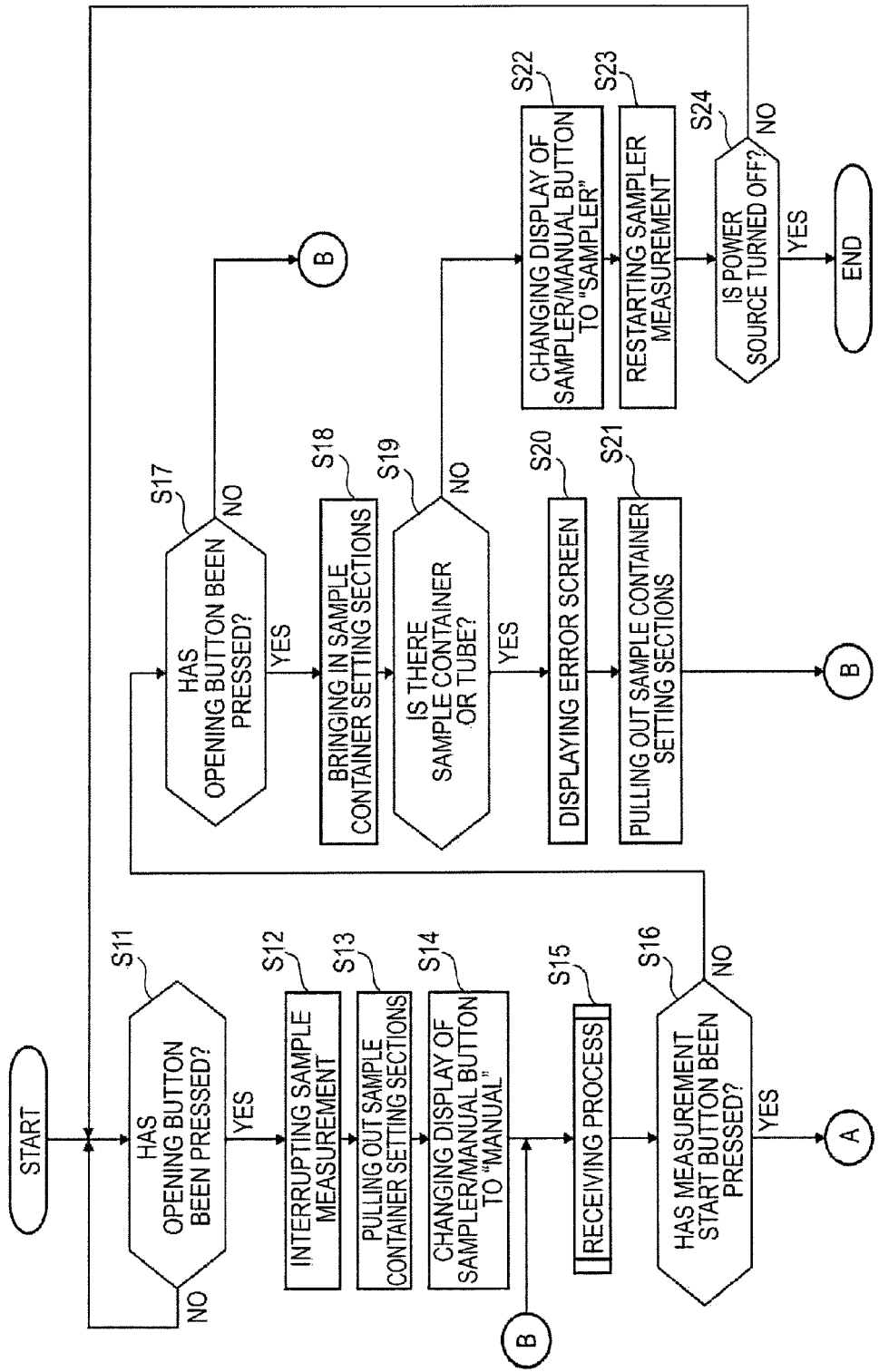
FIG. 9 is a flowchart showing a process of the information processor when the priority sample measurement is performed in the case in which the sampler measurement according to the embodiment is performed.

FIG. 9 is a flowchart showing a process of the information processor 4 when the priority sample measurement is performed in the case in which the sampler measurement is performed.

When the sampler measurement is performed, the CPU 401 of the information processor 4 determines whether or not the opening button 3a of the measuring unit 3 has been pressed (S11). When the opening button 3a is pressed (S11: YES), the CPU 401 interrupts the sampler measurement (S12), and the sample container setting sections 321a and 321b are pulled out forward from the front surface of the measuring unit 3 to be positioned at the priority sample setting positions P5a and P5b, respectively, as shown in FIG. 4C (S13). When the opening button 3a is not pressed (S11: NO), the CPU 401 repeats the determination of S11 and continues the sampler measurement.

Here, in a state in which the sampler measurement is interrupted, a sample container T on the rack transport section 23 of the transport unit 2 is not set in the sample container setting section 321a by the hand section 31. That is, a sample container T on the rack transport section 23 stops on the transport unit 2. Accordingly, the sample container transport section 32 can be used only in the priority sample measurement, and the priority sample measurement can be rapidly performed. Moreover, even in a state in which the sampler measurement is interrupted, a sample container T on the rack transport section 23 may be transported in the transport unit 2 as long as not being set in the sample container setting section 321a. In this case, it is desirable that the position of a sample container T on the rack transport section 23 does not vary significantly so as to rapidly restart the sampler measurement after the end of the priority sample measurement.

When the sample container setting sections 321a and 321b are pulled out (S13), the CPU 401 changes the display of the sampler/manual button D11 of the control menu screen D1 which is displayed on the display section 42 from "SAMPLER" to "MANUAL" (S14). Next, a "receiving process" for receiving an input of a sample number (sample ID) by the input section 41 from a user is performed (S15). The "receiving process" will be described later with reference to FIG. 11.

Next, the CPU 401 determines which one of the measurement start button 3b and the opening button 3a has been pressed by the user. When the measurement start button 3b is pressed (S16: YES), the process advances to a connector A. Accordingly, the process advances to S101 of FIG. 10. When the opening button 3a is pressed (S16: NO, S17: YES), the process advances to S18. When none of the buttons is pressed (S16: NO, S17: NO), the process advances to a connector B. Accordingly, the process returns to S15.

When the user wants to restart the sampler measurement after ending the priority sample measurement, the user takes samples out of the sample container setting sections 321a and 321b, and presses the opening button 3a. When the opening button 3a is pressed (S17: YES), the CPU 401 brings the sample container setting sections 321a and 321b into the measuring unit 3 (S18).

At this time, the CPU 401 determines whether or not a sample container T or a tube M is set in the sample container setting sections 321a and 321b (S19). Whether or not a sample container T is set in the sample container setting section 321a is determined by the barcode unit C as described above, and whether a tube M is set in the sample container setting section 321b is determined by the sensor 34 as described above.

When a sample container T or a tube M is set in the sample container setting sections 321a and 321b (S19: YES), the CPU 401 displays the error screen D31 shown in FIG. 12A on the display section 42 (S20). Furthermore, the CPU 401 pulls out the sample container setting sections 321a and 321b to the front of the measuring unit 3 as shown in FIG. 4C (S21), and the process advances to a connector B. Accordingly, the process returns to S15.

On the other hand, when a sample container T and a tube M are not set in any of the sample container setting sections 321a and 321b (S19: NO), the CPU 401 changes the display of the sampler/manual button D11 from "MANUAL" to "SAMPLER" (S22). In addition, the CPU 401 restarts the sample measurement interrupted in S12 (S23). When a power source of the measuring unit 3 is not turned off (S24: NO), the process returns to S11, and when the power source of the measuring unit 3 is turned off (S24: YES), the process ends.

Figure 10:
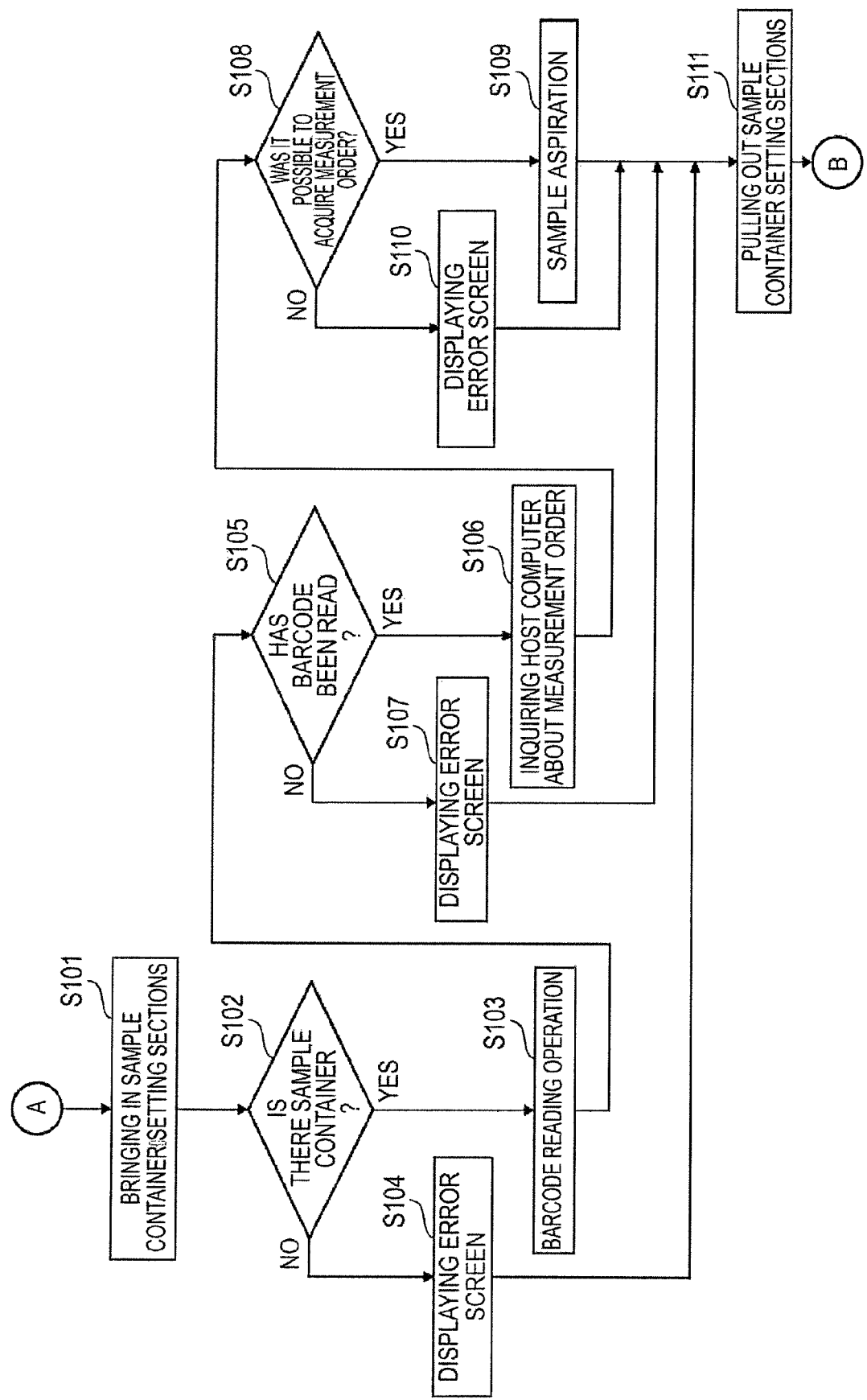
FIG. 10 is a flowchart showing a process of the information processor when the priority sample measurement is performed in the case in which the sampler measurement according to the embodiment is performed.

FIG. 10 is a flowchart showing a process after the connector A.

The CPU 401 of the information processor 4 brings the sample container setting sections 321a and 321b into the measuring unit 3 (S101), and determines whether or not a sample container T is in the sample container setting section 321a (S102).

When it is determined that there is a sample container T (S102: YES), an operation of reading a barcode of the sample container T is performed by the barcode reader C31 (S103). Accordingly, as shown in FIG. 5B, the roller C21 is rotated, and the barcode reader C31 reads the barcode label BL1 during the rotation of the sample container T. On the other hand, when it is determined that there is no sample container T (S102: NO), the CPU 401 displays the error screen D32 shown in FIG. 12B on the display section 42 (S104), and the process advances to S111.

Next, the CPU 401 determines whether or not the barcode has been read from the barcode label BL1 of the sample container T by the process of S103 (S105). When the barcode is read (S105: YES), the CPU 401 inquires the host computer 5 about a measurement order on the basis of the sample ID which is included in the read barcode (S106). On the other hand, when the barcode is not read (S105: NO), the CPU 401 displays the error screen D33 shown in FIG. 12C on the display section 42 (S107), and the process advances to S111.

Examples of the case in which the barcode is not read include a case in which the barcode label BL1 is not adhered to the sample container T, and a case in which even if the barcode label BL1 is adhered to the sample container T, the barcode label BL1 is obliquely adhered or contaminated, and thus the barcode information cannot be appropriately acquired, and the like.

As a result of the inquiry to the host computer 5 about the measurement order, the CPU 401 determines whether or not it was possible to acquire the measurement order from the host computer 5 (S108). When it was possible to acquire the measurement order (S108: YES), the CPU 401 aspirates a sample by the piercer 33 from the sample container T which is set in the sample container setting section 321a (S109), and measures the sample. On the other hand, when it was not possible to acquire the measurement order (S108: NO), the CPU 401 displays the error screen D34 shown in FIG. 12D on the display section 42 (S109), and the process advances to S111.

Thereafter, the CPU 401 pulls out the sample container setting sections 321a and 321b to the front of the transport unit 2 (S111), and the process advances to the connector B. Accordingly, the process returns to S15 of FIG. 9.

Figure 11:
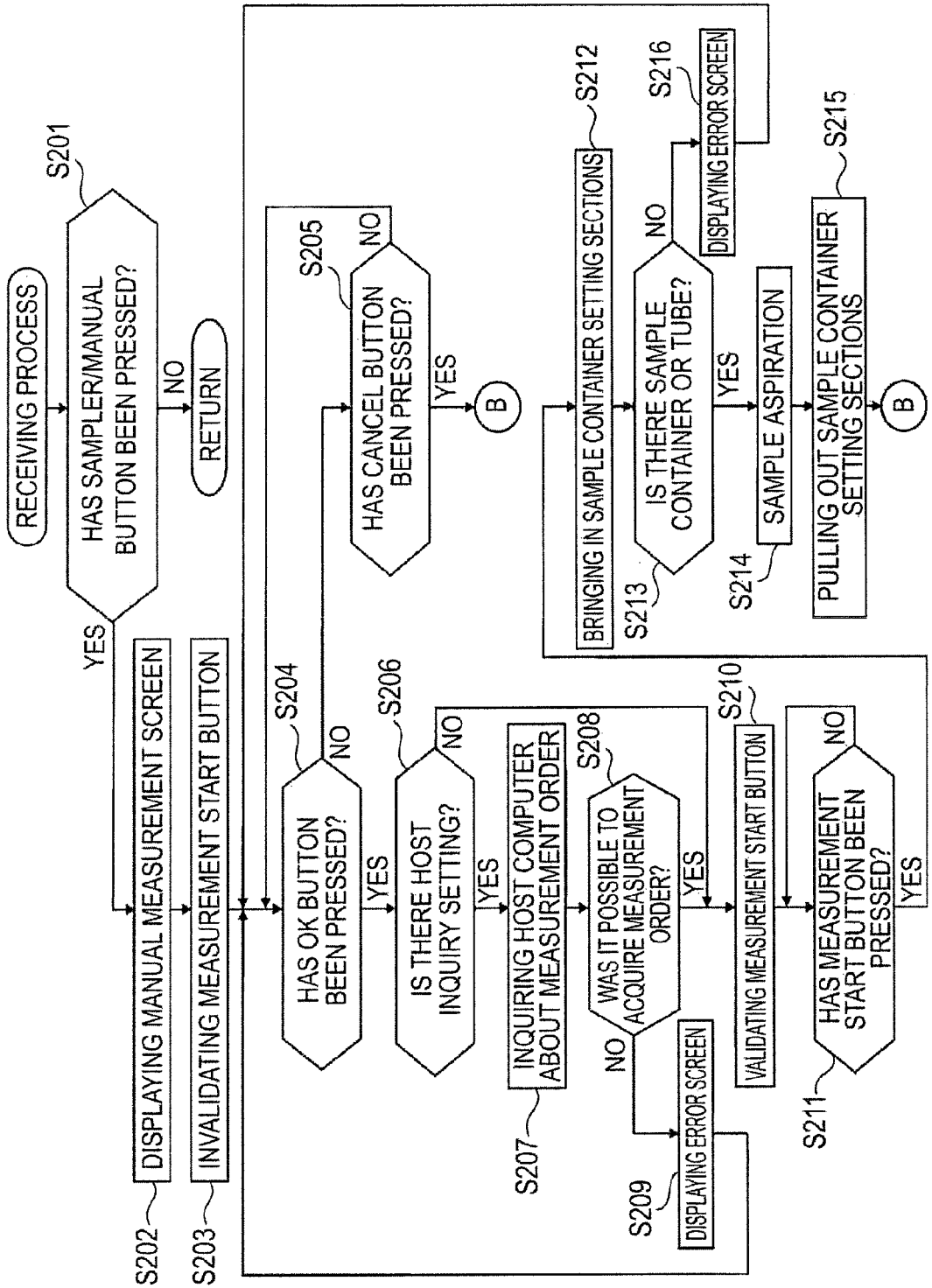
FIG. 11 is a flowchart showing a receiving process according to the embodiment.

FIG. 11 is a flowchart showing the receiving process. In the receiving process, the sampler/manual button D11 becomes active.

The CPU 401 of the information processor 4 determines whether or not the sampler/manual button D11 has been pressed (S201). When the sampler/manual button D11 is not pressed (S201: NO), the receiving process ends. When the sampler/manual button D11 is pressed (S201: YES), the CPU 401 displays the manual measurement screen D2 on the display section 42 (S202), and invalidates the measurement start button 3b disposed on the front surface of the measuring unit 3 (S203). The user inputs information of a sample to be subjected to the priority sample measurement in the respective regions in the manual measurement screen D2.

Next, it is determined which one of the OK button D25 and the cancel button D26 of the manual measurement screen D2 has been pressed by the user (S204, S205). When the OK button D25 is pressed (S204: YES), the process advances to S206. When the cancel button D26 is pressed (S204: NO, S205: YES), the process returns to the connector B. Accordingly, the process returns to S15 of FIG. 9. When none of the buttons is pressed (S204: NO, S205: NO), the process returns to S204.

When the OK button D25 is pressed (S204: YES), the CPU 401 determines whether or not the check box of the host inquiry display region D24 of the manual measurement screen D2 has been checked (S206). When the box is checked (S206: YES), the CPU 401 inquires the host computer 5 about a measurement order on the basis of the sample number (sample ID) which is input to the sample number display region S21 (S207). On the other hand, when the box is not checked (S206: NO), the process advances to S210.

As a result of the inquiry to the host computer 5 about the measurement order, the CPU 401 determines whether or not it was possible to acquire the measurement order from the host computer 5 (S208). When it was not possible to acquire the measurement order (S208: NO), the error screen D34 shown in FIG. 12D is displayed on the display section 42 (S209), and the process returns to S204. On the other hand, when it was possible to acquire the measurement order (S208: YES), the CPU 401 validates the measurement start button 3b (S210).

Next, the CPU 401 puts the process on hold until the measurement start button 3b is pressed (S211). The user sets a sample container T or a tube M in the sample container setting section 321a or 321b before pressing the measurement start button 3b. When the measurement start button 3b is pressed (S211: YES), the CPU 401 brings the sample container setting sections 321a and 321b into the measuring unit 3 (S212), and determines whether or not a sample container T or a tube M is in the sample container setting section 321a or 321b (S213).

When it is determined that there is a sample container T or a tube M (S213: YES), the CPU 401 positions the sample container T or the tube M at the aspirating position P4, aspirates a sample by the piercer 33 (S214), and measures the sample. Thereafter, the sample container setting sections 321 and 321b are pulled out to the front of the measuring unit 3 (S215) as shown in FIG. 4C, and the process advances to the connector B. Accordingly, the process returns to S15 of FIG. 9.

On the other hand, when it is determined that there is no sample container T or tube M (S213: NO), the error screen D32 shown in FIG. 12B is displayed on the display section 42 (S216), and the process returns to S204. Further, when the sample container T and the tube M are set in both of the sample container setting sections 321a and 321b, the determination result is NO in S213.

According to this embodiment, as shown in FIGS. 9 and 10, in the case in which the priority sample measurement is performed, when the measurement start button 3b is pressed in a state in which a sample container T is set in the sample container setting section 321a, the barcode information is read from the sample container T, and the aspiration of the sample contained in the sample container T is started. In addition, when the sampler/manual button D11 is pressed in a state in which a sample container T is set in the sample container setting section 321a, the manual measurement screen D2 is displayed. When the measurement start button 3b is pressed after the input of a sample number and the like via the manual measurement screen D2, the aspiration of the sample contained in the sample container T is started without an operation of reading the barcode of the sample container T. In this manner, a user can appropriately select between the input of barcode information by the barcode reader C31 and the input of a sample number and the like via the manual measurement screen D2, and thus the identification data of the sample can be smoothly input.

Further, also in a state in which the tube M is set in the sample container setting section 321b, the manual measurement screen D2 is displayed when the sampler/manual button D11 is pressed. When the measurement start button 3b is pressed after the input of a sample number and the like via the manual measurement screen D2, the aspiration of the sample contained in the Tube M is started without an operation of reading the barcode of the Tube M. In addition, even when a sample container T having a barcode label BL1 which cannot be appropriately read is used, a user can input the information such as a sample number by operating the sampler/manual button D11.

In addition, according to this embodiment, as shown in FIG. 11, when information such as a sample number is appropriately input to the manual measurement screen D2 in the receiving process, the priority sample measurement is performed without the reading by the barcode reader C31. Accordingly, the priority sample processing can be rapidly performed on the basis of the information such as a sample number input to the manual measurement screen D2.

Figure 12A:
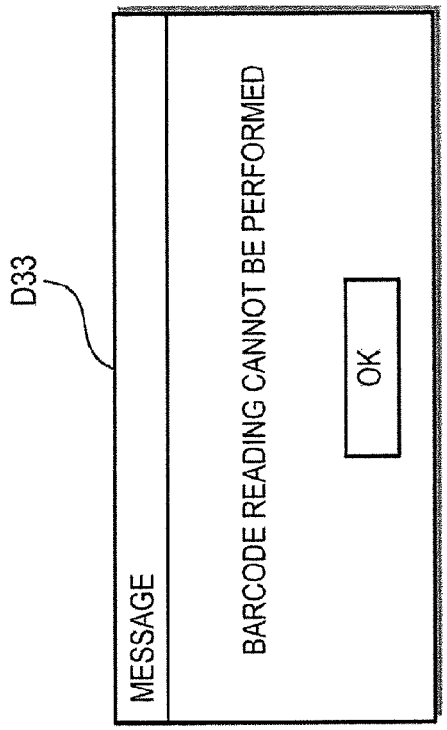
FIG. 12 shows error screens which are displayed on the display section of the information processor according to the embodiment.
Figure 12C:
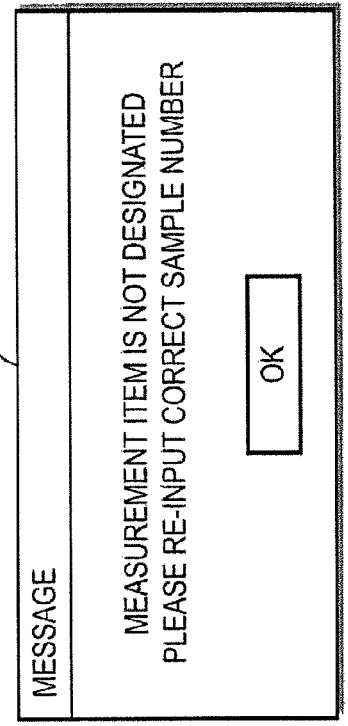
Figure 12B:
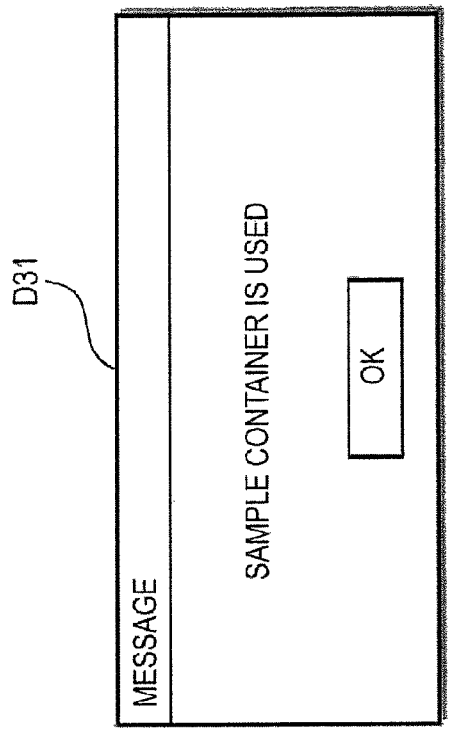
Figure 12D:
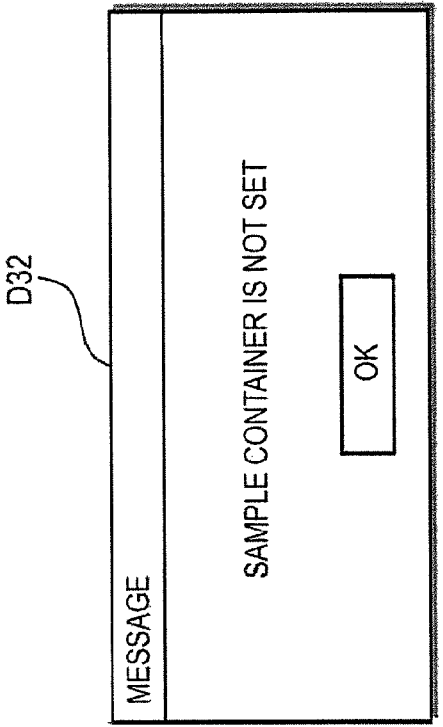

In addition, according to this embodiment, when the barcode is not read by the barcode reader C31, the error screen D33 shown in FIG. 12C is displayed. In addition, when the measurement order is not acquired on the basis of the sample number input to the manual measurement screen D2, the error screen D34 shown in FIG. 12D is displayed. Accordingly, a user can know that the barcode cannot be read and the measurement order cannot be acquired.

In addition, according to the invention, the measurement start button 3b is invalidated from when the manual measurement screen D2 is displayed to when the input of identification data is completed (S206 of FIG. 11: NO, S208: YES). Accordingly, the priority sample measurement is not started by mistake during the input of a sample number and the like by the manual measurement screen D2.

In addition, according to this embodiment, when the opening button 3a is pressed during the sampler measurement, the sampler measurement is interrupted, and the display of the sampler/manual button D11 is changed to "MANUAL". In this manner, the sampler/manual button D11 can display the manual measurement screen D2 after the interruption of the sampler measurement, and thus it is possible to prevent the incorrect input via the manual measurement screen D2.

The embodiments of the invention have been described as above, but are not limited thereto.

For example, in the above-described embodiments, blood is exemplified as a measurement target. However, urine may be a measurement target. That is, the invention can also be applied to sample processing systems which examine urine and can be further applied to clinical sample processing apparatuses which examine other clinical samples.

In addition, in the above-described embodiments, the receiving process shown in FIG. 9 is performed between S14 and S16. However, the invention is not limited thereto, and the receiving process may be performed between S16 and S17, and may be performed immediately after the determination result "NO" is obtained in S17. That is, the receiving process may be performed at any time if it is performed before the reading by the barcode reader C31.

In addition, in the above-described embodiments, in FIG. 10, when the barcode is not read through the reading operation by the barcode reader C31 (S105: NO), the error screen D33 is displayed, and then the process returns to S15 of FIG. 9. However, the invention is not limited thereto, and when the barcode is not read (S105: NO), an input of a sample number and the like by the manual measurement screen D2 may be received.

Figure 13:
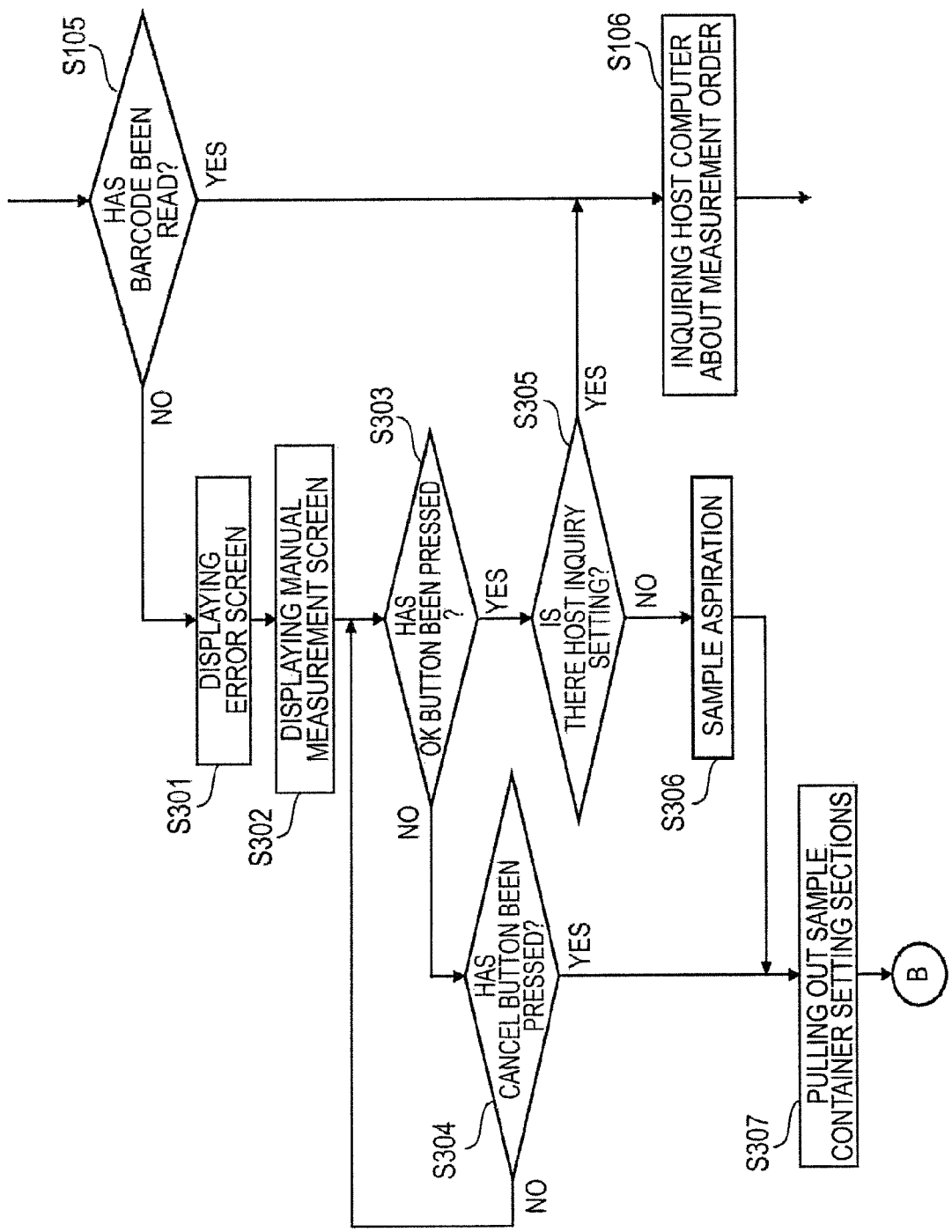
FIG. 13 is a modified example of the flowchart showing the process of the information processor when the priority sample measurement is performed in the case in which the sampler measurement according to the embodiment is performed.

FIG. 13 is a flowchart when the process between the process of S105 and the process of S106 of FIG. 10 is changed.

When the barcode is not read (S105: NO), the CPU 401 of the information processor 4 displays the error screen D33 on the display section 42 (S301). Next, the CPU 401 displays the manual measurement screen D2 shown in FIG. 8C on the display section 42 (S302). A user inputs a sample number (sample ID) and the like of a sample container T whose barcode is not read to the respective regions in the manual measurement screen D2.

Next, it is determined which one of the OK button D25 and the cancel button D26 of the manual measurement screen D2 has been pressed by the user. When the OK button D25 is pressed (S303: YES), the process advances to S306, and when the cancel button D26 is pressed (S303: NO, S304: YES), the process advances to S207. When none of the buttons is pressed (S303: NO, S304: NO), the process returns to S303.

When the OK button D25 is pressed (S303: YES), the CPU 401 determines whether or not the check box of the host inquiry display region D24 of the manual measurement screen D2 has been checked (S305). When the box is checked (S305: YES), the process advances to S106. On the other hand, when the box is not checked (S305: NO), the sample is aspirated from the sample container T (S306), and the sample is measured. Thereafter, the sample container setting sections 321a and 321b are pulled out to the front of the measuring unit 3 (S307), and the process advances to the connector B. Accordingly, the process returns to S15 of FIG. 9.

When such a process is performed, there is no need to repeat the reading operation until the sample ID is properly read by the barcode reader C31, and the priority sample measurement is performed on the basis of the sample number and the like input to the manual measurement screen D2. Accordingly, the priority sample measurement can be rapidly performed.

In addition, in the above-described embodiments, when the sampler measurement is performed, the barcode readers B31 and C31 sequentially read a barcode label BL1 of a sample container T. Here, when the barcode readers B31 and C31 can not read a barcode, a user may be allowed to input a sample number and the like. That is, a user may be allowed to input a sample number and the like of a sample container T whose barcode can not be read, via the manual measurement screen D2 in place of the display of an error screen. Accordingly, even when the barcode reading is sequentially performed in the sampler measurement, a sample number and the like can be easily input using the manual measurement screen D2.

In the embodiments of the invention, various modifications can be made appropriately in the scope of the technical idea shown in the claims.

What is claimed is:

1. A sample analyzer comprising:
   a sample container setting section for receiving a sample container;
   a barcode unit for reading identification data (ID) of a sample from a sample container set on the sample container setting section;
   an aspirator that aspirates the sample in the sample container set on the sample container setting section;
   a specimen preparation section that mixes the aspirated sample and a reagent to prepare a measurement specimen;
   a detecting section that measures the specimen prepared by the specimen preparation section;

a measurement start button;

an information processor connected with a host computer and configured to receive an operation of the measurement start button; and a display section for displaying under control of the information processor a manual measurement screen including a sample number display region for inputting an ID of a sample and a discrete display region for displaying one or more measurement items, an input section for designating the one or more measurement items in the discrete display region;

wherein the information processor is configured to control the aspirator to aspirate the sample from the sample container and control the specimen preparation section and the detecting section to perform measurements on the measurement items designated in the discrete display region in response to the measurement start button being operated, the ID of the sample being received in the sample number display region of the manual measurement screen, and the measurement items of the sample being designated in the discrete display region of the manual measurement screen, and the information processor is configured to control the barcode unit to read an ID of a sample from a sample container, inquire the host computer to obtain a measurement order which corresponds to the ID, control the aspirator to aspirate the sample from the sample container and control the specimen preparation section and the detecting section to perform measurement based on the obtained measurement order in response to the measurement start button being operated and the ID of the sample not being received in the sample number display region of the manual measurement screen.

2. The sample analyzer of claim 1, wherein, the information processor is configured to output a notification to prompt a user to input an ID in the sample number display region of the manual measurement screen when the information processor fails to obtain a measurement order in the inquiry to the host computer.

3. The sample analyzer of claim 1, further comprising a driving section for transferring the sample container setting section between an aspiration position corresponding to the aspirator and a set position where the sample container setting section is located outwardly from the sample analyzer to receive a sample container set by a user.

4. The sample analyzer of claim 1, further comprising a detector for detecting a sample container set on the sample container setting section.

5. The sample analyzer of claim 1, wherein the manual measurement screen further includes a host inquiry display region, and the information processor is configured to inquire the host computer to obtain a measurement order which corresponds to the ID received in the sample number display region, when the ID of the sample has been received in the sample number display region and the inquiry display region has been operated, and the information processor is configured to control the aspirator to aspirate the sample from the sample container and control the specimen preparation section and the detecting section to perform measurements based on the measurement order obtained from the host computer.

6. The sample analyzer of claim 1, wherein the barcode unit includes a barcode reader and rollers, and the information processor is configured to control the rollers to come into contact with a sample container on the sample container setting section and to rotate with the sample container, and the information processor is configured to control the barcode reader to read barcode while rotating the sample container.

7. The sample analyzer of claim 1, wherein the discrete display region includes a plurality of checkboxes corresponding to a plurality of measurement items.

* * * * *